United States Patent
Bando et al.

(10) Patent No.: US 7,659,411 B2
(45) Date of Patent: Feb. 9, 2010

(54) PROCESS FOR PRODUCING 2-ACYLTHIOPHENE COMPOUND

(75) Inventors: Seiji Bando, Hyogo (JP); Syuzo Satake, Hyogo (JP); Hirokazu Kagano, Hyogo (JP)

(73) Assignee: Sumitomo Seika Chemicals Co., Ltd., Hyogo (JP)

( * ) Notice: Subject to any disclaimer, the term of this patent is extended or adjusted under 35 U.S.C. 154(b) by 510 days.

(21) Appl. No.: 10/579,734

(22) PCT Filed: Dec. 13, 2004

(86) PCT No.: PCT/JP2004/018569

§ 371 (c)(1),
(2), (4) Date: May 18, 2006

(87) PCT Pub. No.: WO2005/058866

PCT Pub. Date: Jun. 30, 2005

(65) Prior Publication Data

US 2007/0149787 A1 Jun. 28, 2007

(30) Foreign Application Priority Data

Dec. 17, 2003 (JP) ............................. 2003-419362

(51) Int. Cl.
- *C07D 333/28* (2006.01)
- *C07D 333/22* (2006.01)
- *A61K 31/38* (2006.01)
- *A01N 43/06* (2006.01)

(52) U.S. Cl. ........................... 549/81; 549/70; 514/438; 514/448

(58) Field of Classification Search ................... 549/70, 549/81; 514/438, 448
See application file for complete search history.

(56) References Cited

U.S. PATENT DOCUMENTS

| | | | | |
|---|---|---|---|---|
| 2,458,512 A | * | 1/1949 | Hartough et al. | 549/70 |
| 2,458,519 A | | 1/1949 | Kosak | |
| 2,711,414 A | * | 6/1955 | Norton | 549/70 |
| 6,274,741 B1 | * | 8/2001 | Choudary et al. | 548/540 |

FOREIGN PATENT DOCUMENTS

| | | |
|---|---|---|
| EP | 0 248 393 | 12/1987 |
| EP | 1-138-681 | 10/2001 |
| JP | A-61-143374 | 7/1986 |
| JP | A-2001-288166 | 10/2001 |
| WO | WO 01/32593 | 5/2001 |
| WO | WO 0132593 A1 * | 5/2001 |

OTHER PUBLICATIONS

Chakrabarti et. al., Reactive Polymers, 1993, Elsevier Science, vol. 20, pp. 1-45.*

Supplementary European Search Report dated Sep. 15, 2008 in corresponding European patent application No. 04806930.6-1211 (and English translation).
Choudary et al., *Selective acetylation of 5-numbered aromatic heterocycle compounds using metal-exchanged clay catalysts*, Catalysis Letters, vol. 76, No. 3-4, 2001.
*Environmentally Friendly Catalysts for Acylation Reactions*, M. Campanati, F. Fazzini, G. Fornasari, A. Tagliani, A. Vaccari: In Chemical Industries (1998), vol. 75, pp. 307-318.
*The Nation-H-catalyzed Acylation of Thiophene with Acid Anhydrides*, Hisatoshi Konishi, Kazuhiro Suetsugu, Tamon Okano, Jitsuo Kiji; Bulletin of the Chemical Society of Japan (1982), vol. 55, No. 3. pp. 957-958.
*Acylation Studies in the Thiophene and Furan Series. III. Natural and Synthetic Silica-Metal Oxide Catalysts*, H. Hartough, A. Kosak, J. Sardella in *J. Am. Chemical Society*, (1947)vol. 69, pp. 1014-1016.
Office Action dated Mar. 7, 2008 in corresponding Chinese Patent Application No. 200480035125.2 (and English translation).

* cited by examiner

*Primary Examiner*—Sreeni Padmanabhan
*Assistant Examiner*—Sarah Pihonak
(74) *Attorney, Agent, or Firm*—Posz Law Group, PLC

(57) ABSTRACT

The present invention provides a process for producing a 2-acylthiophene compound which has a low content of the 3-isomer generated as a by-product, the process comprising reacting a thiophene compound represented by formula (1):

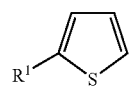

(1)

wherein $R^1$ is a hydrogen atom, a $C_{1-6}$ alkyl group, a phenyl group, or a halogen atom, with at least one member selected from the group consisting of acid anhydrides represented by formula (2):

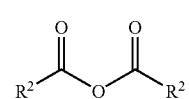

(2)

wherein $R^2$ is a $C_{1-6}$ alkyl group or a phenyl group, and acid halides represented by formula (3):

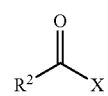

(3)

wherein $R^2$ is as defined above and X is a halogen atom, in the presence of a solid acid catalyst at a temperature less than 75° C. in the absence of solvent, thus producing a 2-acylthiophene compound represented by formula (4):

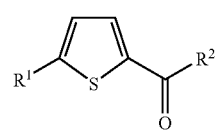

(4)

wherein $R^1$ and $R^2$ are as defined above.

2 Claims, No Drawings

PROCESS FOR PRODUCING 2-ACYLTHIOPHENE COMPOUND

TECHNICAL FIELD

The present invention relates to a process for producing a 2-acylthiophene compound. 2-acylthiophene compounds are useful as starting materials and intermediates for preparing pharmaceuticals and the like.

BACKGROUND ART

In the synthesis of pharmaceuticals, reductions in the amount of impurities are strongly required in view of enhancing safety of the pharmaceuticals that are final products. In particular, isomers that are by-products in the reaction steps conducted in preparing a pharmaceutical usually resemble each other in physical properties, so that the separation for purification is not easy. Therefore, isomers in the starting materials and intermediates produced by preceding steps may cause various side reactions in the subsequent reactions conducted in preparing the pharmaceutical, which results in a final product containing high contents of various side reaction products as impurities. Therefore, the isomer content of starting materials used for preparing a pharmaceutical is often strictly controlled in units of 0.1 wt. %.

Likewise for the production of 2-acylthiophene compounds that are useful as starting materials and intermediates for preparing pharmaceuticals and the like, a process of production with a low isomer content is similarly desired. Further, a process of production thereof without using solvent, in particular, organic solvent, is strongly desired from the viewpoint of environmental concerns and production costs.

Conventionally, various processes for producing 2-acylthiophene compounds in the absence of solvent are known. Examples of such known processes include a process comprising reacting thiophene and an acid anhydride using activated clay under reflux (J. Am. Chem. Soc., 69, 1014, (1947)) and a process comprising reacting thiophene and acetic anhydride using an ion exchange resin at 75° C. to 125° C. (U.S. Pat. No. 2,711,414).

However, products obtained by conventional processes for producing 2-acylthiophene compounds contain comparatively large amounts of by-product 3-isomers, i.e., have an isomer content of about 1 wt. % and furthermore, separation thereof is not easy. Therefore, when the compound is to be used as a starting material or an intermediate for preparing a pharmaceutical or the like, it has been necessary to perform purification using a multiple-plate distillation column, etc.

For example, in the production of 2-acetylthiophene, when distillation is performed during the post-production process to separate the 3-isomer to thereby purify the product, simple distillation is virtually ineffective and it is necessary to use a multiple-plate distillation column, etc. For example, even when a 50 theoretical plate distillation column is used in a distillation process for purification to obtain 2-acetylthiophene with a 3-isomer content of 0.5 wt. % from 2-acetylthiophene with a 3-isomer content of 0.9 wt. %, the purification yield was only about 70%. Therefore, also because it is not easy to separate the 3-isomer produced, a process of production with a low by-product 3-isomer content is desired.

DISCLOSURE OF INVENTION

Problems to be Solved by the Invention

An object of the present invention is to provide a process for producing a 2-acylthiophene compound which has a low content of the 3-isomer generated as a by-product.

Means for Solving the Problems

The present invention provides processes for producing 2-acylthiophene compounds as described below.

1. A process for producing a 2-acylthiophene compound comprising reacting a thiophene compound represented by formula (1):

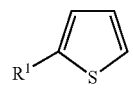

(1)

wherein $R^1$ is a hydrogen atom, a $C_{1-6}$ alkyl group, a phenyl group, or a halogen atom, with at least one member selected from the group consisting of acid anhydrides represented by formula (2):

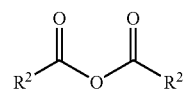

(2)

wherein $R^2$ is a $C_{1-6}$ alkyl group or a phenyl group, and acid halides represented by formula (3):

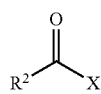

(3)

wherein $R^2$ is as defined above and X is a halogen atom, in the presence of a solid acid catalyst at a temperature less than 75° C. in the absence of solvent, thus producing a 2-acylthiophene compound represented by formula (4):

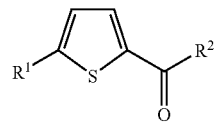

(4)

wherein $R^1$ and $R^2$ are as defined above.

2. The process according to item 1 wherein the solid acid catalyst is at least one member selected from the group consisting of zeolites, activated clays, and cation exchange resins.

3. The process according to item 1 or 2 wherein the solid acid catalyst is used in an amount of 0.1 to 50 parts by weight per 100 parts by weight of the thiophene compound.

The present invention is described below in detail.

The thiophene compound used in the invention is a compound represented by the above formula (1). In formula (1), $R^1$ is a hydrogen atom, a $C_{1-6}$ alkyl group, a phenyl group, or a halogen atom.

Examples of $C_{1-6}$ alkyl groups include methyl, ethyl, n-propyl, isopropyl, n-butyl, tert-butyl, n-pentyl, n-hexyl, and the like.

Examples of halogens include chlorine, bromine, iodine, and the like.

Examples of thiophene compounds represented by the above formula (1) include thiophene, 2-methylthiophene, 2-ethylthiophene, 2-n-propylthiophene, 2-isopropylthiophene, 2-n-butylthiophene, 2-tert-butylthiophene, 2-n-pentylthiophene, 2-n-hexylthiophene, 2-phenylthiophene, 2-chlorothiophene, 2-bromothiophene, 2-iodothiophene, and the like.

Such thiophene compounds can be produced by known methods. Of the thiophene compounds represented by the above formula (1), those wherein $R^1$ is a $C_{1-6}$ alkyl group can be produced, for example, by a method comprising reducing the corresponding acyl thiophene. Of the thiophene compounds represented by the above formula (1), the compound wherein $R^1$ is a phenyl group can be produced, for example, by a method comprising reacting a 2-halothiophene with phenylboronic acid using a palladium catalyst. Further, of the thiophene compounds represented by the above formula (1), those wherein $R^1$ is a halogen atom can be produced, for example, by a method comprising reacting thiophene with a molecular halogen, an N-halogenosuccinimide, or the like.

The acid anhydride used in the invention is a compound represented by the above formula (2). In formula (2), $R^2$ is a $C_{1-6}$ alkyl group or a phenyl group.

Examples of $C_{1-6}$ alkyl groups include methyl, ethyl, n-propyl, isopropyl, n-butyl, isobutyl, sec-butyl, tert-butyl, n-pentyl, tert-pentyl, n-hexyl, and the like.

Examples of acid anhydrides represented by the above formula (2) include acetic anhydride, propionic anhydride, butyric anhydride, isobutyric anhydride, valeric anhydride, isovaleric anhydride, 2-methylbutyric anhydride, pivalic anhydride, hexanoic anhydride, 2,2-dimethylbutyric anhydride, heptanoic anhydride, benzoic anhydride, and the like. Such acid anhydrides can be produced, for example, by heating the corresponding acid with a dehydrating agent.

The acid halide used in the invention is a compound represented by the above formula (3). In formula (3), $R^2$ is as defined in formula (2), and X is a halogen atom.

Examples of halogen atoms include fluorine, chlorine, bromine, and the like.

Examples of acid halides represented by the above formula (3) include acetyl fluoride, acetyl chloride, acetyl bromide, propionyl chloride, n-butyryl chloride, isobutyryl chloride, valeryl chloride, isovaleryl chloride, 2-methylbutyryl chloride, pivaloyl chloride, n-hexanoyl chloride, 2,2-dimethylbutyryl chloride, n-heptanoyl chloride, benzoyl chloride, and the like. Such acid halides can be prepared, for example, by reacting the corresponding acid with a thionyl halide.

In the present invention, such acid anhydrides or acid halides may be used singly, or an acid anhydride and an acid halide of formulae (2) and (3) wherein each $R^2$ is the same may be used in combination.

To reduce the amount of unreacted residual thiophene compound and to achieve an effect commensurate with the amount used, the at least one member selected from the group consisting of acid anhydrides and acid halides as described above is preferably used in an amount of 0.4 to 10 moles, and more preferably 0.5 to 3 moles, per mole of the thiophene compound.

The solid acid catalyst used in the invention is not particularly limited, and examples thereof include zeolites, activated clays, and cation exchange resins. Usable cation exchange resins are not particularly limited, and examples thereof include perfluorosulfonic acid polymers, sulfonic acid polymers, and the like. Such solid acid catalysts can be used singly or as a combination of two or more kinds.

To allow the reaction to proceed smoothly and to achieve an effect commensurate with the amount used, the solid acid catalyst is preferably used in an amount of 0.1 to 50 parts by weight, and more preferably 1 to 30 parts by weight, per 100 parts by weight of the thiophene compound.

The reaction temperature is less than 75° C., preferably at least −10° C. but less than 75° C., and more preferably 10° C. to 60° C. When the reaction temperature is less than −10° C., the reaction rate tends to be slow and it may take a long time to complete the reaction. When the reaction temperature is 75° C. or higher, large amounts of isomers may be generated. The reaction time is preferably 1 to 100 hours, although it is difficult to generalize because the reaction time varies depending on the reaction temperature. In the present invention, since the reaction proceeds in the absence of a solvent, it is unnecessary to use a solvent.

Examples of methods of isolating the desired target 2-acylthiophene compound from the reaction mixture include distillation methods, methods comprising adding water and separating the reaction mixture, followed by concentrating the organic layer obtained by the separation and then adding a solvent to the precipitated crystals to perform recrystallization, and like methods.

The 2-acylthiophene compound thus obtained is a compound represented by the above formula (4). In formula (4), $R^1$ is as defined in formula (1), and $R^2$ is as defined in formulae (2) and (3).

Examples of 2-acylthiophene compounds represented by the above formula (4) include 2-acetylthiophene, 2-propionylthiophene, 2-butyrylthiophene, 2-isobutyrylthiophene, 2-valerylthiophene, 2-isovalerylthiophene, 2-(2-methyl)butyrylthiophene, 2-pivaloylthiophene, 2-hexanoylthiophene, 2-(2,2-dimethyl)butyrylthiophene, 2-heptanoylthiophene, 2-benzoylthiophene, 2-acetyl-5-methylthiophene, 2-acetyl-5-ethylthiophene, 2-acetyl-5-n-propylthiophene, 2-acetyl-5-isopropylthiophene, 2-acetyl-5-n-butylthiophene, 2-acetyl-5-tert-butylthiophene, 2-acetyl-5-n-pentylthiophene, 2-acetyl-5-n-hexylthiophene, 2-acetyl-5-phenylthiophene, 2-acetyl-5-chlorothiophene, 2-acetyl-5-bromothiophene, 2-acetyl-5-iodothiophene, and the like.

Effects of the Invention

According to the present invention, a 2-acylthiophene compound whose by-product 3-isomer content is not more than 0.5 wt. % can be easily obtained industrially at low cost.

BEST MODE FOR CARRYING OUT THE INVENTION

Examples of the present invention and comparative examples are given below to illustrate the invention in more detail, but the scope of the invention is not limited to these examples.

EXAMPLE 1

80 g of activated clay (product of Nacalai Tesque, Inc.) and 347.1 g (3.4 moles) of acetic anhydride were introduced into a 1-liter 4-necked flask equipped with a stirrer, condenser, thermometer, and dropping funnel. 286.1 g (3.4 moles) of thiophene was added dropwise at 25° C. to 35° C. over 1 hour. After the dropwise addition, the reaction was allowed to proceed at 30° C. for 96 hours. After the reaction, the activated clay was separated by filtration to give a dark brown filtrate. The filtrate was subjected to distillation to remove unreacted thiophene, acetic anhydride, and by-product acetic acid, thus giving 278.8 g (2.2 moles) of 2-acetylthiophene. The yield of 2-acetylthiophene was 65% based on thiophene.

The 3-isomer, i.e., 3-acetylthiophene content was determined by high-performance liquid chromatography. The 3-acetylthiophene content of the resulting 2-acetylthiophene product was 0.3 wt. %. The following conditions were used to perform the high-performance liquid chromatography: column: TSKgel ODS-80TS 4.6 mm φ×250 mm (product of Tosoh Corporation), mobile phase: 0.05 wt. % aqueous potassium dihydrogen phosphate solution (phosphoric acid pH=3.7)/acetonitrile=75/25 (V/V), flow rate: 1 ml/min, column thermostat temperature: 30° C., and detector: UV220 nm.

EXAMPLE 2

2.5 g of a perfluorosulfonic acid polymer (product of N.E. Chemcat corporation, trade name: SAC-13) which is a cation exchange resin, and 25.5 g (0.25 moles) of acetic anhydride were introduced into a 100 ml 4-necked flask equipped with a stirrer, condenser, thermometer, and dropping funnel. 21.0 g (0.25 moles) of thiophene was added dropwise at 25° C. to 30° C. over 30 minutes. After the dropwise addition, the reaction was allowed to proceed at 30° C. for 40 hours. After the reaction, the perfluorosulfonic acid polymer was separated by filtration to give a dark brown filtrate. The filtrate was subjected to distillation to remove unreacted thiophene, acetic anhydride, and by-product acetic acid, thus giving 24.3 g (0.19 moles) of 2-acetylthiophene. The yield of 2-acetylthiophene was 77% based on thiophene. The 3-isomer content was determined in the same manner as in Example 1. The 3-acetylthiophene content of the resulting 2-acetylthiophene product was 0.5 wt. %.

EXAMPLE 3

2.5 g of a sulfonic acid polymer (product of SIGMA-ALDRICH, trade name: DOWEX-DR2030) which is cation exchange resin and 25.5 g (0.25 moles) of acetic anhydride were introduced into a 100 ml 4-necked flask equipped with a stirrer, condenser, thermometer, and dropping funnel. 21.0 g (0.25 moles) of thiophene was added dropwise at 20° C. to 25° C. over 1 hour. After the dropwise addition, the reaction was allowed to proceed at 40° C. for 45 hours. After the reaction, the sulfonic acid polymer was separated by filtration to give a dark brown filtrate. The filtrate was subjected to distillation to remove unreacted thiophene, acetic anhydride, and by-product acetic acid, thus giving 26.4 g (0.21 moles) of 2-acetylthiophene. The yield of 2-acetylthiophene was 84% based on thiophene. The 3-isomer content was determined in the same manner as in Example 1. The 3-acetylthiophene content of the resulting 2-acetylthiophene product was 0.4 wt. %.

EXAMPLE 4

5.9 g of a zeolite (product of Tosoh Corporation, trade name: HSZ-360HUA) and 25.5 g (0.25 moles) of acetic anhydride were introduced into a 100 ml 4-necked flask equipped with a stirrer, condenser, thermometer, and dropping funnel. 21.0 g (0.25 moles) of thiophene was added dropwise at 25° C. to 35° C. over 1 hour. After the dropwise addition, the reaction was allowed to proceed at 30° C. for 96 hours. After the reaction, the zeolite was separated by filtration to give a dark brown filtrate. The filtrate was subjected to distillation to remove unreacted thiophene, acetic anhydride, and by-product acetic acid, thus giving 19.4 g (0.15 moles) of 2-acetylthiophene. The yield of 2-acetylthiophene was 62% based on thiophene. The 3-isomer content was determined in the same manner as in Example 1. The 3-acetylthiophene content of the resulting 2-acetylthiophene product was 0.5 wt. %.

EXAMPLE 5

5.9 g of activated clay (product of Nacalai Tesque, Inc.) and 21.0 g (0.25 moles) of thiophene were introduced into a 100 ml 4-necked flask equipped with a stirrer, condenser, thermometer, and dropping funnel. 19.6 g (0.25 moles) of acetyl chloride was added dropwise at 25° C. to 35° C. over 2 hours. After the dropwise addition, the reaction was allowed to proceed at 30° C. for 48 hours. After the reaction, the activated clay was separated by filtration to give a black filtrate. The filtrate was subjected to distillation to remove unreacted thiophene and acetyl chloride, thus giving 18.3 g (0.15 moles) of 2-acetylthiophene. The yield of 2-acetylthiophene was 58% based on thiophene. The 3-isomer content was determined in the same manner as in Example 1. The 3-acetylthiophene content of the resulting 2-acetylthiophene product was 0.4 wt. %.

EXAMPLE 6

5.9 g of activated clay (product of Nacalai Tesque, Inc.) and 56.6 g (0.25 moles) of benzoic anhydride were introduced into a 100 ml 4-necked flask equipped with a stirrer, condenser, thermometer, and dropping funnel. 21.0 g (0.25 moles) of thiophene was added dropwise at 55° C. to 65° C. over 1 hour. After the dropwise addition, the reaction was allowed to proceed at 60° C. for 72 hours. After the reaction, the activated clay was separated by filtration to give a dark brown filtrate. The filtrate was subjected to distillation to remove unreacted thiophene, benzoic anhydride, and by-product benzoic acid, thus giving 26.0 g (0.14 moles) of 2-benzoylthiophene. The yield of 2-benzoylthiophene was 55% based on thiophene. The 3-isomer content was determined in the same manner as in Example 1. The 3-benzoylthiophene content of the resulting 2-benzoylthiophene product was 0.5 wt. %.

EXAMPLE 7

5.9 g of activated clay (product of Nacalai Tesque, Inc.) and 25.5 g (0.25 moles) of acetic anhydride were introduced into a 100 ml 4-necked flask equipped with a stirrer, condenser, thermometer, and dropping funnel. 24.6 g (0.25 moles) of 2-methylthiophene was added dropwise at 2520 C. to 35° C. over 1 hour. After the dropwise addition, the reaction was allowed to proceed at 30° C. for 48 hours. After the reaction, the activated clay was separated by filtration to give a black filtrate. The filtrate was subjected to distillation to remove unreacted 2-methylthiophene, acetic anhydride, and by-product acetic acid, thus giving 23.5 g (0.17 moles) of 2-acetyl-5-methylthiophene. The yield of 2-acetyl-5-methylthiophene was 67% based on 2-methylthiophene. The 3-isomer content was determined in the same manner as in Example 1. The 3-acetyl-5-methylthiophene content of the resulting 2-acetyl-5-methylthiophene product was 0.5 wt. %.

EXAMPLE 8

5.9 g of activated clay (product of Nacalai Tesque, Inc.) and 25.5 g (0.25 moles) of acetic anhydride were introduced into a 100 ml 4-necked flask equipped with a stirrer, condenser, thermometer, and dropping funnel. 29.6 g (0.25 moles) of 2-chlorothiophene was added dropwise at 45° C. to 55° C. over 1 hour. After the dropwise addition, the reaction was allowed to proceed at 50° C. for 72 hours. After the reaction, the activated clay was separated by filtration to give a dark brown filtrate. The filtrate was subjected to distillation to remove unreacted 2-chlorothiophene, acetic anhydride, and by-product acetic acid, thus giving 20.9 g (0.13 moles) of 2-acetyl-5-chlorothiophene. The yield of 2-acetyl-5-chlorothiophene was 52% based on 2-chlorothiophene. The 3-isomer content was determined in the same manner as in Example 1. The 3-acetyl-5-chlorothiophene content of the resulting 2-acetyl-5-chlorothiophene product was 0.5 wt. %.

COMPARATIVE EXAMPLE 1

11.3 g of 85 wt. % phosphoric acid and 273.6 g (2.7 moles) of acetic anhydride were introduced into a 1-liter 4-necked flask equipped with a stirrer, condenser, thermometer, and dropping funnel. 225.5 g (2.7 moles) of thiophene was added dropwise at 25° C. to 35° C. over 30 minutes. After the dropwise addition, the reaction was allowed to proceed at 30° C. for 60 hours. After the reaction, 100 g of 10 wt. % aqueous ammonia was added dropwise and stirred, and the reaction mixture was separated to give a black oily layer. The oily layer was subjected to distillation to remove unreacted thiophene, acetic anhydride, and by-product acetic acid, thus giving 172.4 g (1.4 moles) of 2-acetylthiophene. The yield of 2-acetylthiophene was 51% based on thiophene. The 3-isomer content was determined in the same manner as in Example 1. The 3-acetylthiophene content of the resulting 2-acetylthiophene product was 1.0 wt. %.

COMPARATIVE EXAMPLE 2

5.8 g of activated clay (product of Nacalai Tesque, Inc.) and 25.5 g (0.25 moles) of acetic anhydride were introduced into a 100 ml 4-necked flask equipped with a stirrer, condenser, thermometer, and dropping funnel. 21.0 g (0.25 moles) of thiophene was added dropwise at 75° C. to 85° C. over 10 minutes. After the dropwise addition, the reaction was allowed to proceed at 100° C. under reflux for 5 hours. After the reaction, the activated clay was separated by filtration to give a black filtrate. The filtrate was subjected to distillation to remove unreacted thiophene, acetic anhydride, and by-product acetic acid, thus giving 22.1 g (0.18 moles) of 2-acetylthiophene. The yield of 2-acetylthiophene was 70% based on thiophene. The 3-isomer content was determined in the same manner as in Example 1. The 3-acetylthiophene content of the resulting 2-acetylthiophene product was 0.9 wt. %.

The invention claimed is:

1. A process for producing a 2-acylthiophene compound comprising reacting a thiophene compound represented by formula (1):

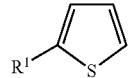

(1)

wherein $R^1$ is a hydrogen atom, a $C_{1-6}$ alkyl group, a phenyl group, or a halogen atom, with at least one member selected from the group consisting of acid anhydrides represented by formula (2):

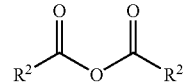

(2)

wherein $R^2$ is a $C_{1-6}$ alkyl group or a phenyl group, and acid halides represented by formula (3):

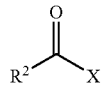

(3)

wherein $R^2$ is defined above and X is a halogen atom, in the presence of a cation exchange resin at a temperature of 10° C. to 60° C. in the absence of solvent, thus producing a 2-acylthiophene compound represented by formula (4):

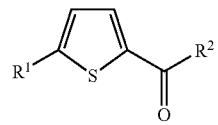

(4)

wherein $R^1$ and $R^2$ are as defined above.

2. The process according to claim 1 wherein the cation exchange resin is used in an amount of 0.1 to 50 parts by weight per 100 parts by weight of the thiophene compound.

* * * * *